United States Patent [19]

Reher et al.

[11] Patent Number: 5,254,002
[45] Date of Patent: Oct. 19, 1993

[54] ORTHODONTIC PLASTIC BRACKET

[75] Inventors: James F. Reher, Pomona; Farrokh Farzin-Nia, Inglewood, both of Calif.

[73] Assignee: Ormco Corporation, Glendora, Calif.

[21] Appl. No.: 682,261

[22] Filed: Apr. 8, 1991

[51] Int. Cl.⁵ .................................. A61C 3/00
[52] U.S. Cl. .................................. 433/8
[58] Field of Search ........................ 433/8, 9, 16

[56] References Cited

U.S. PATENT DOCUMENTS

| 2,908,974 | 10/1959 | Stifter | 433/16 |
| 3,469,314 | 9/1969 | Pearlman | 433/8 |
| 3,775,850 | 12/1973 | Northcutt | 433/16 |
| 3,922,787 | 12/1975 | Fischer et al. | 433/15 |
| 3,930,311 | 1/1976 | Andrews | 433/8 |
| 3,964,165 | 6/1976 | Stahl | 433/8 |
| 4,050,156 | 9/1977 | Chasanoff et al. | 433/8 |
| 4,107,844 | 8/1978 | Kurz | 433/8 |
| 4,186,488 | 2/1980 | Wallshein | 433/8 |
| 4,249,897 | 2/1981 | Anderson | 433/8 |
| 4,299,569 | 11/1981 | Frantz | 433/8 |
| 4,302,532 | 11/1984 | Wallshein | 433/8 |
| 4,353,692 | 10/1982 | Karrakussoglu | 433/16 |
| 4,674,978 | 6/1987 | Acevedo | 433/8 |
| 4,717,341 | 1/1988 | Goldberg et al. | 433/9 |
| 4,850,865 | 7/1989 | Napolitano | 433/8 |
| 5,078,596 | 1/1992 | Carberry et al. | 433/9 |
| 5,141,436 | 8/1992 | Orlowski et al. | 433/226 |

Primary Examiner—John J. Wilson
Attorney, Agent, or Firm—Wood, Herron & Evans

[57] ABSTRACT

An orthodontic bracket and method of making same. The bracket comprises a main body portion made of a rigid plastic material having a filler for improved strength. The bracket further includes a rigid reinforcement molded into the body for strengthening the archwire slot. The method comprises forming at least one insert in a blank sheet of metal, forming the insert to its final configuration, placing the insert in a mold cavity and forming the bracket around the insert, removing the bracket from the mold and separating the bracket from the sheet of metal at a predetermined point.

46 Claims, 8 Drawing Sheets

ORTHODONTIC PLASTIC BRACKET

The present invention is directed to orthodontic brackets and, more particularly, to aesthetically pleasing orthodontic brackets made of a plastic material.

BACKGROUND OF THE INVENTION

In the field of orthodontics there has been an increasing demand for brackets that are visually aesthetic. In response to this need, various materials have been suggested for making orthodontic brackets. Various ceramic materials have been used in making orthodontic brackets. However, orthodontic brackets made from ceramic materials are quite brittle and thus are subject to fracture. Additionally, ceramic materials are substantially more expensive to produce than typical prior art metal brackets.

Plastic materials have also been suggested for use in making orthodontic brackets. However, plastic orthodontic brackets have been found to be unsatisfactory due to their inability to provide the appropriate strength necessary over the long periods of time for which the orthodontic brackets are typically used. In order to improve the strength of a plastic orthodontic bracket, it has been suggested to provide metal reinforcement such as illustrated in U.S. Pat. No. 3,930,311, issued Jan. 6, 1976 and U.S. Pat. No. 4,107,844, issued Aug. 22, 1978 and/or the use of metal inserts in the archwire slot as shown in U.S. Pat. No. 4,299,569, issued Nov. 10, 1981 and U.S. Pat. No. 4,302,532, issued Nov. 24, 1981. In the '311 patent there is disclosed an orthodontic bracket which uses a sheet metal stiffening core embedded in the plastic which extends in the direction substantially perpendicular to the longitudinal axis of the archwire slot and is designed so as to reinforce the wings projecting on either side of the bracket. The '844 patent used metal reinforcements embedded within the bracket. The '569 patent discloses a metal insert which extends along the length of the archwire slot and comprises a generally U-shaped cross-section configuration. In the '532 patent, various metal insert configurations are disclosed for placement in the archwire slot. While the metal inserts of the '569 and '532 patents provide improved strength to the archwire slot, the overall strength of the bracket is substantially limited by the plastic material of the orthodontic bracket. Over time, the plastic tends to deform due to the constant force being applied to the bracket by the orthodontic archwire. Additionally, due to the configuration of the insert, the insert can be pulled out in a direction away from the bonding base of the bracket.

It has also been suggested in the prior art to make brackets of a plastic material reinforced with a filler. However, over time, the glass filled plastic bracket tends to distort and, thus, loose their effectiveness as an orthodontic appliance.

Applicants have invented an improved plastic orthodontic bracket which minimizes or eliminates many of the problems of the prior art.

SUMMARY OF THE INVENTION

In one aspect of the present invention there is provided an orthodontic bracket having a body portion made of a rigid plastic material having a filler for improved strength. A high strength reinforcing insert is molded in the body portion of the bracket which forms at least a portion of the archwire slot.

In another aspect of the present invention there is provided an orthodontic bracket having a body portion made of a rigid plastic material having a filler for improved strength. A high strength reinforcing insert is provided which forms at least a portion of the archwire slot. The insert is configured so as to allow a portion of the plastic body to flow therethrough and form the remaining portion of the archwire slot.

In yet another aspect of the present invention there is provided a method of making a plastic orthodontic bracket having a metal insert for reinforcing the archwire slot. The method comprises the steps of:
a) providing a metal blank in a predetermined shape having a main body portion and at least one insert section connected by a narrow gate section;
b) bending the insert section so as to form a generally U-shape insert having a bottom section and pair of sidewall support sections;
c) placing the metal blank in a mold and causing plastic to be formed around the inset section; and
d) removing the blank from said mold and cutting the bracket formed around the insert section from the blank at the gate section.

DETAILED DESCRIPTION OF THE INVENTION

Figure 1:
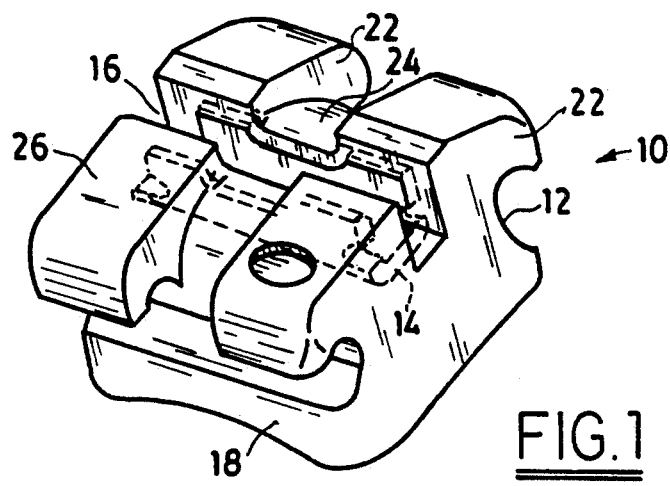
FIG. 1 is a perspective view of an orthodontic bracket made in accordance with the present invention.
Figure 5:
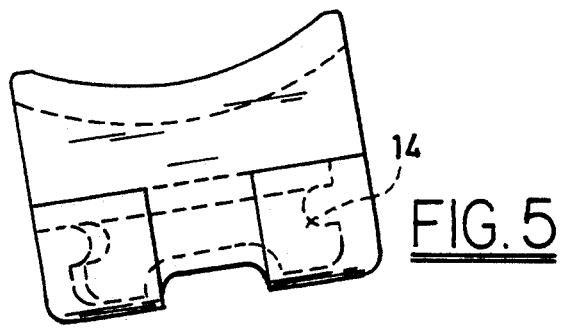
FIG. 5 is a back elevational view of the orthodontic bracket of FIG. 2.
Figure 2:
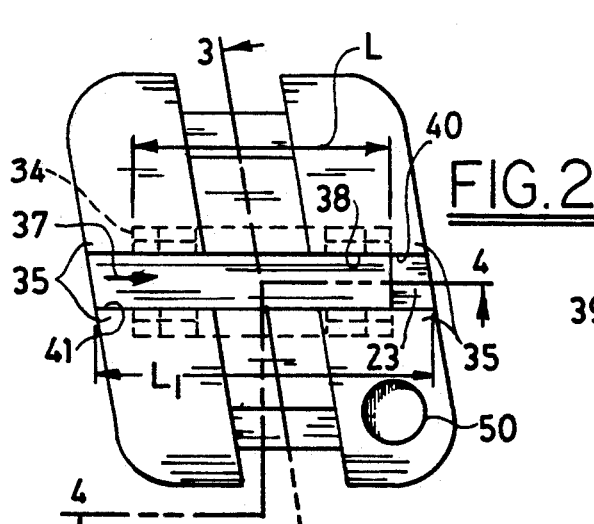
FIG. 2 is a top plan view of the orthodontic bracket of FIG. 1.

Referring to FIGS. 1-6, there is illustrated an orthodontic bracket 10 having a main body portion 12 and reinforcing insert 14 embedded therein such that the body portion 12 and insert 14 combined together to form an orthodontic archwire slot 16 which is designed to receive an orthodontic archwire in the same manner as typical prior art orthodontic brackets. The main body portion 12 includes a base portion 18 having a bonding base surface 20 which is designed to be secured to a tooth in any conventional manner, for example, by an appropriate orthodontic cement/adhesive. Body portion 12 further includes a pair of orthodontic tiewings 22 which extend from the base portion 18 and are connected by a connecting portion 24. The tiewings 22 function substantially in the same manner as other orthodontic tiewings present in conventional orthodontic brackets. As is typical with prior art orthodontic brackets, the tiewings 22 overhang the base portion 18 to allow proper ligation of an orthodontic archwire in the archwire slot 16.

The body portion 12 is made of a plastic material such that the body portion 12 can be easily formed in a mold. Preferably, the body portion 12 is made of a substantial transparent, translucent or tooth colored plastic material. Applicants have found that the body portion 12 should have a minimum amount of rigidity. The plastic is reinforced with a sufficient amount of reinforcement fiber such that the tensile strength of the material is at least about 13,000 psi and flex modulus of about $8 \times 10^5$ psi, preferably of at least about 15,000 psi. In order to improve the rigidity and strength of the main body portion 12, a glass filler is provided. In the particular embodiment illustrated, the main body portion 12 is made out of a clear polycarbonate plastic and is filled with a fiber reinforcement material. In order to provide the desired strength, the plastic is filled with a chopped glass fiber reinforcement of at least 15% by weight. Preferably, the plastic is reinforced with about 20% (by weight) glass fiber reinforcement. Applicants have found that filler in excess of 20% provides increased stiffness. This is done at the sacrifice of aesthetics. Fillers greater than about 20% (by weight) tend to reduce the clarity of a substantially transparent bracket. Applicants have found that a polycarbonate plastic having 20% (by weight) glass fiber reinforcement, sold by LNP Engineering Plastic, having product code LNP-DF1004, works quite satisfactorily.

Figure 3:
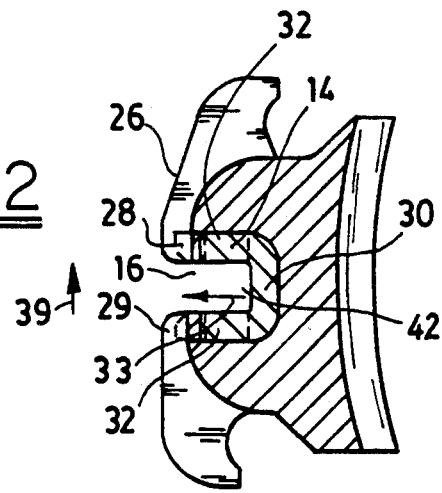
FIG. 3 is a side cross-sectional view of the bracket of FIG. 2 taken along line 3—3.
Figure 4:
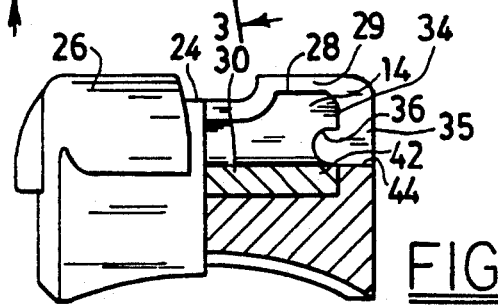
FIG. 4 is a front elevational view, partially in cross-section, of the orthodontic bracket of FIG. 2 as taken along line 4—4.
Figure 11:
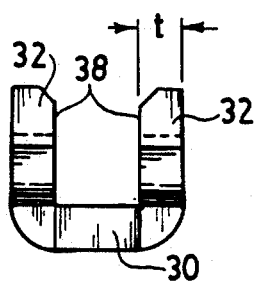
FIG. 11 is a side elevational view of the insert of FIG. 10.
Figure 10:
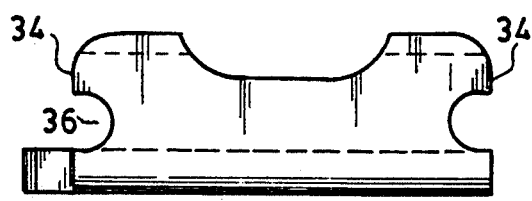
FIG. 10 is a front elevational view of the insert of FIG. 8.
Figure 12:
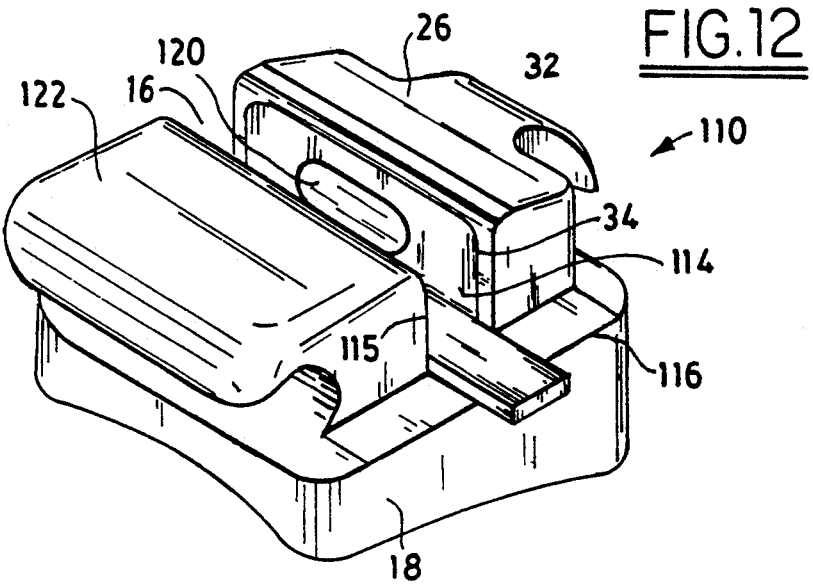
FIG. 12 is a perspective view of a modified orthodontic bracket made in accordance with the present invention.
Figure 13:
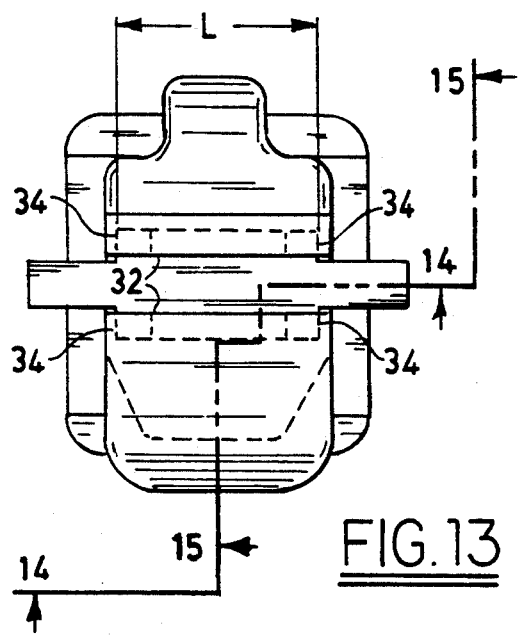
FIG. 13 is a top plan view of the orthodontic bracket of FIG. 12.
Figure 15:
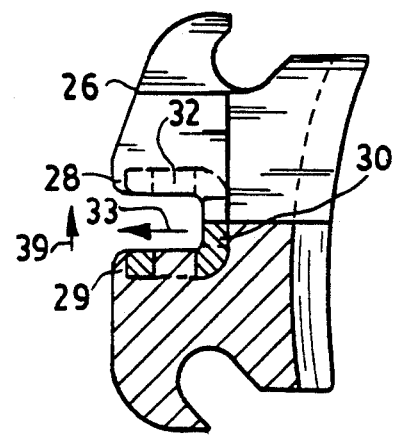
FIG. 15 is side elevational view, partially in cross-section, of the orthodontic bracket of FIG. 13 as taken along line 15—15.
Figure 14:
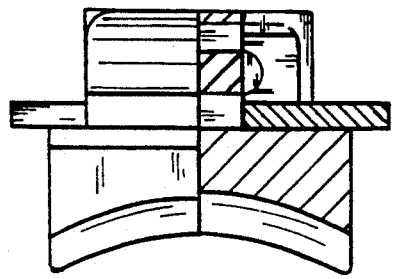
FIG. 14 is a front elevational view, partially in cross-section, of the orthodontic bracket of FIG. 13 as taken along line 14—14.
Figure 16:
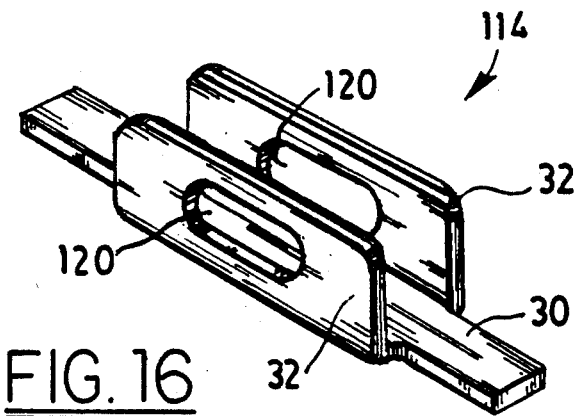
FIG. 16 is a perspective view of the insert of the orthodontic bracket of FIG. 12.
Figure 17:
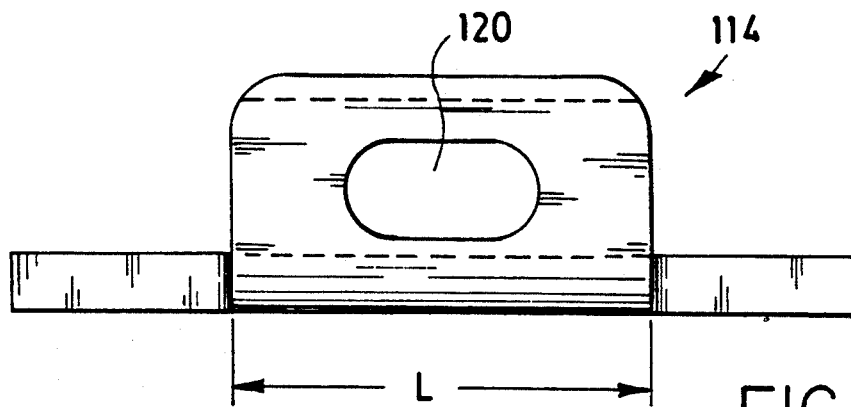
FIG. 17 is a front elevational view of the insert of FIG. 16.
Figure 18:
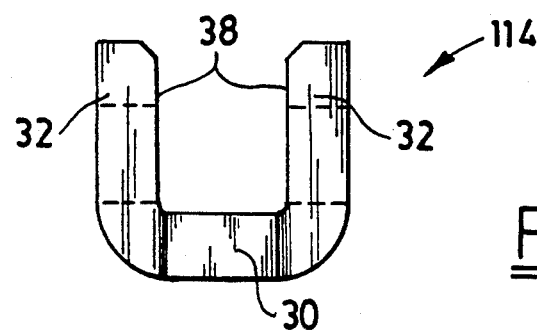
FIG. 18 is a side elevational view of the insert of FIG. 16.

While the filled plastic body portion 12 improves the overall strength of the bracket it is still necessary to further strengthen the archwire slot 20, thus requiring the use of a reinforcing insert 14 made of a high strength material. In the particular embodiment illustrated the insert 14 is made of metal, more particularly in the embodiment illustrated, insert 14 is ma stainless steel ¼ hard having a thickness of about 0.010 inches (0.254 mm). The insert 14 is preferably designed such that it does not extend to the top surface 26 of body portion 12. Thus, as best seen in FIG. 4, the top surface 28 of insert 14 extends below the top surface 26 of body portion 12 such that a cover portion 29 of the body portion 12 extends over the top surface 28 of insert 14. In the particular embodiment illustrated, cover portion 29 extends above insert a distance of about 0.005 to 0.01 inches (0.127 to 0.254 mm). However, this may be varied as desired. Cover portion 29 assists in resisting forces tending to pull insert 14 vertically outward from the bracket portion 12 that may be applied by the archwire secured in slot 16. Additionally, by having the top surface 28 of insert below the top surface 26 the aesthetic appearance of the bracket is further improved as the metal insert 14 becomes less distinct in appearance to the viewer. The insert 14 comprises a bottom wall 30 having a pair of upstanding sidewalls 32 extending from axially opposite edges so as to form a substantially U-shaped cross-sectional configuration as best seen in FIGS. 3 and 11. The insert 14 has a length L which is preferably less than the length L1 of the archwire slot 16 such that ends 34 of sidewalls 32 are also not exposed, thus resulting in the ends 34 being covered by side portion 35 of body portion 12. The side portions 35 improves the appearance of the bracket 10 in the same manner as cover portion 29, and also provides means to prevent the insert 14 from moving in the axial direction of slot 16. In the particular embodiment illustrated, side portion 35 has a thickness in the range of about 0.005 to 0.01 inches (0.127 to 0.254 mm). As with cover portion 29, side portion 35 may vary in thickness as desired. The ends 34 have notched out sections 36 which allows the plastic body portion 12 to flow therein which provides further strength in resisting movement of insert 14 in body portion 12, both in the longitudinal direction (as represented by arrow 37 in FIG. 2) of the slot 16 and in the vertical direction with respect of the base of slot 16 (as represented by arrow 33 in FIG. 3). By covering the edges of the insert 14 with cover portions 29 and 35, leakage of fluid between the insert 14 and body portion 12 is eliminated and/or minimized. Applicants have found that this improves the aesthetical appearance of the bracket. When liquid seeps between the insert and bracket, a dark discoloration can occur which can substantially change any aesthetic qualities the bracket may have. This also minimizes any hygienic problem that can occur due to the leakage between the insert 14 and body portion 12. Since the insert 14 is molded in body portion 12, the lateral movement is also restricted as indicated by arrow 39 in FIG. 3. Thus, the body portion 12 resists movement of the insert 14 in all directions which force may be applied by the archwire.

The inside surface 38 of sidewalls 32 of insert 14 is substantially flush with the adjacent surface 40 of body portion 12 such that the inside surface 38 and 40 combine together to form the sidewalls 41 of the archwire slot 16. Likewise the bottom surface 42 of bottom wall 30 of insert is substantially flush with the adjacent surface 44 of body 12 so as to form the bottom surface 23 of the archwire slot 16. As can best be seen in FIG. 4, the configuration of the insert 14 in the connecting portion 24 of body portion 12 is such that it is be below the top surface 26 of the bracket 10. The insert 14 strengthens the slot 16 so that the forces being applied by the archwire will be more evenly transmitted to the bracket 10. Additionally, the metal insert 14 reduces the coefficient of friction between the archwire and the plastic body 12, thus allowing the archwire to easily slide in slot 16 during treatment of the patient. The insert is designed to have a sufficient rigidity to resist permanent deformation caused by the application of typical forces applied by an archwire placed therein, generally forces up to about 2-3 lb range.

Figure 6:
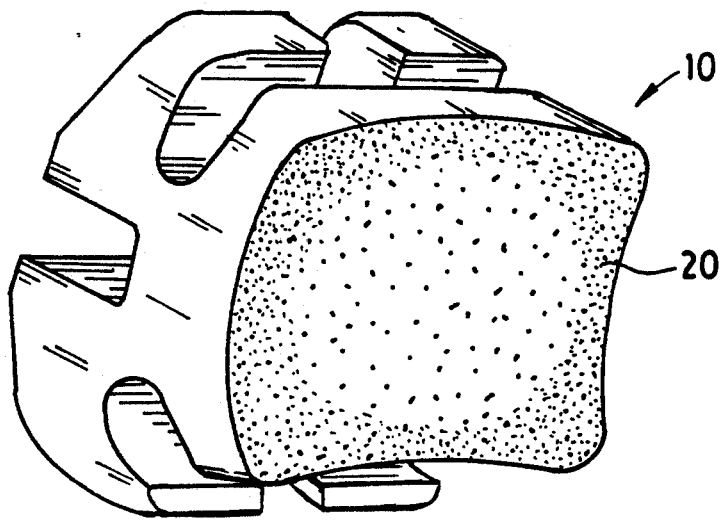
FIG. 6 is a perspective view of the orthodontic bracket of FIG. 1 as seen from the backside.

Referring to FIG. 6, there is illustrated the orthodontic bracket 10 wherein the bonding base surface 20 has been roughened so as to provide more surface area to improve the bond strength between the bracket and tooth. In the particular in the embodiment illustrated, the bonding base surface 20 has been roughened by an electrode placed against the contact surface and energized a sufficient time period so as to provide a roughened appearance. Alternatively, the roughened surface may be simply designed into the mold in which bracket 10 is to be formed.

Figure 7:
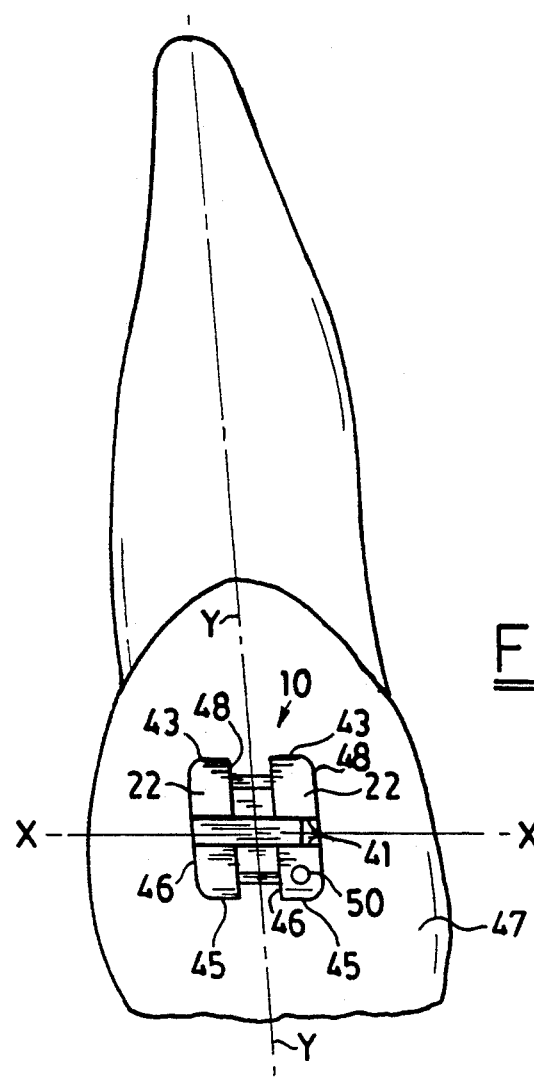
FIG. 7 is a front elevational view of the orthodontic bracket of FIG. 1 as mounted to the tooth.
Figure 8:
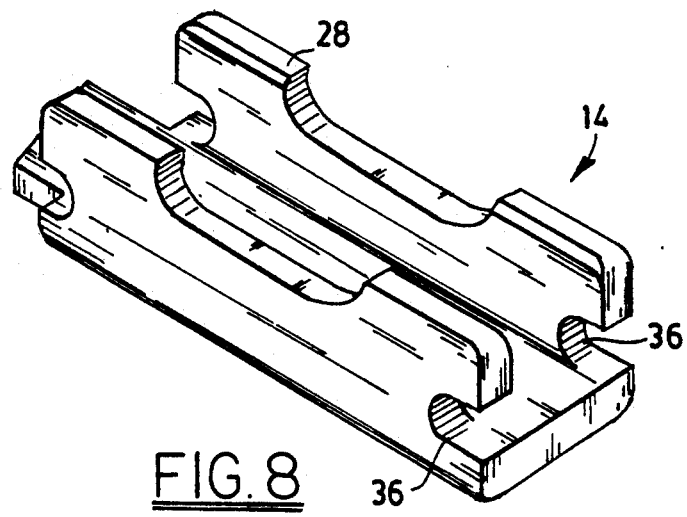
FIG. 8 is a perspective view of the insert of the orthodontic bracket of FIG. 1.
Figure 9:
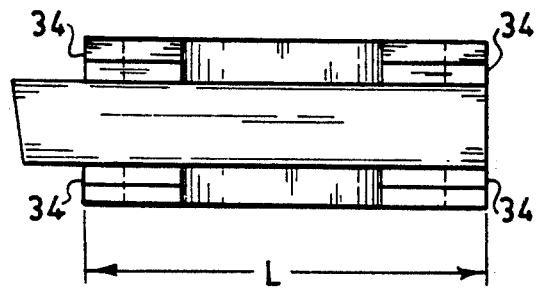
FIG. 9 is a top plan view of the insert of FIG. 8.

The bracket 10 is preferably configured such that the top surface has features which assists in placement of the bracket on the tooth 47. Referring to FIG. 7, the bracket 10 is provided with at least one reference edge which is substantially parallel to longitudinal axis Y—Y of the tooth 47 and one reference edge is substantially parallel to the occlusal plane of the patient when the bracket is mounted to the tooth 47. In the particular embodiment illustrated, this is accomplished by the particular configuration of the tiewings 22. In the particular embodiment illustrated, the sidewalls 41 of the archwire slot 16 are substantially parallel to the occlusal plane of the patient as illustrated in FIG. 7 wherein line X—X represents the occlusal plane. Preferably, as illustrated, the top edge 43 and bottom edge 45 of tiewings 22 are also substantially parallel to the occlusal plane. It should be noted that the edges 43, and 45 need not be completely straight, it being only necessary that they have a shape such that an overall reference plane is provided which is substantially parallel to the occlusal plane X—X. The tiewings 22 each have a mesial edge 46 and distal edge 48; at least one of the edges 46, 48 being substantially parallel to the longitudinal axis Y—Y of the tooth. Preferably, as illustrated, both edges 46 and 48 are substantially parallel to the longitudinal axis Y—Y of the tooth. However, it should be noted it is not essential that both edges 46 and 48 be parallel to each other or exactly parallel to the Y—Y axis. It is necessary only that tiewings 22 are such that their overall configuration provides at least one generally longitudinal reference feature which can be aligned with the longitudinal axis Y—Y of the tooth 47. Preferably, as illustrated, the orthodontic bracket 10 has a generally overall rhomboidal shape. This alignment feature becomes even more important with aesthetic-type brackets. These brackets can be more difficult to align due to their transparent or tooth-like color. If desired, edges 41,43,44,46,48 may be visibly enhanced for ease of alignment, for example, by the placement of a water-soluble colored stain along the edges, or the surface of the tiewings such as described in copending application Ser. No. 437,199, filed Nov. 16, 1989, which is hereby incorporated by reference.

The orthodontic bracket 10 is also provided with an indicator means for identifying the type of bracket being supplied and the position in which is to be applied. In the particular embodiment illustrated, a substantially circular recess 50 is provided which extends a small distance below surface of the bracket. Recess 50 may be color coded to identify the position of the tooth, for example, a central lateral cuspid or bicuspid position. Additionally, the position of the recess 50 on the tiewings can further assist in identifying the position and how the bracket is to be placed on the tooth. For example, the recess 50 may be designed to be oriented toward to the gingival side of the tooth.

The connecting portion 24 is designed such that the bracket 10 can be used substantially as a twin wing orthodontic bracket as presently done in prior art. However, since the bracket 10 is made of a plastic material, it is desired to maintain a sufficient amount of strength in the slot between tiewing 22. In order to do this, the connecting portion 24 preferably has a generally rounded section so that the substantial portion of the slot between the tiewings 22 are supported as best seen in FIG. 3. However, the top surface of connecting portion 24 is disposed a sufficient amount below the adjacent tiewing so that ligation of various appliances may be adequately secured to the bracket.

Referring to FIGS. 12-18, there is illustrated a modified bracket 110 made in accordance with the present invention. Bracket 110 is similar to bracket 10, identical numbers indicating like parts. Bracket 110 is of the single wing type construction, thus only a single tiewing 122 is provided in the body portion 12.

Reinforcing metal insert 114 in bracket 110 functions in the same manner as insert 14 of bracket 10. The insert 114, in the particular embodiment illustrated, is configured so as to provide a recess 120 in each sidewall 32 so that some of the body portion flows therethrough and forms a portion of the archwire slot 16. In the particular embodiment illustrated, each side wall 32 has a generally U-shaped configuration with the open end of the U-shaped configuration being connected to the bottom wall 30 of insert 114. The insert 114 is structured such that the tops of the sidewalls 32 do not extend over the top surface 26 of the bracket 110. Likewise, the ends 34 of the sidewall inserts do not extend past the edges 115 of the body 12. In the particular embodiment illustrated, the bottom wall 30 of insert 114 extends past the edges 115,116 of the body 12 and base portion 18. The bottom wall 30 of insert 114 which extends past the slot 16 and body portion 12 can be used to provided rotation control of the archwire placed in the bracket 110. The recess 120 of insert 114 provides a locking feature to prevent the insert from moving either along the axis of the slot or vertically therein. Since the insert is molded in the bracket, the insert is restricted in its movement within the body portion 12.

Figure 19:
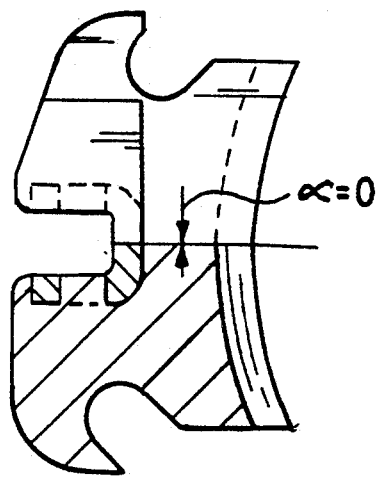
FIG. 19 is a side elevational view of the bracket of FIG. 1 having zero degree torque in the base.
Figure 20:
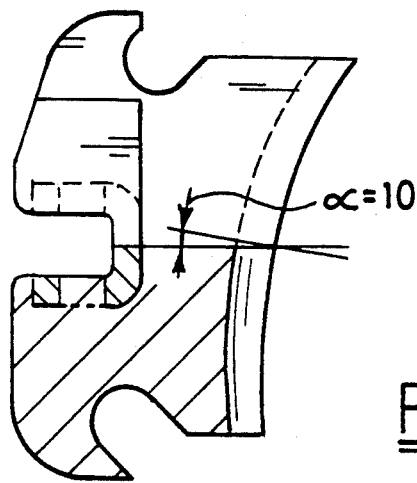
FIG. 20 is a view similar to FIG. 19 illustrating the bracket with +10° torque in the base.
Figure 21:
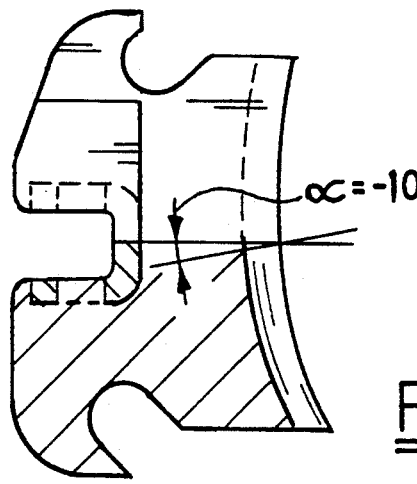
FIG. 21 is a view similar to FIG. 19 illustrating the bracket with −10° torque in the base.

Since the brackets 10,110 may be conveniently and easily formed in a mold, torque may be provided in the base portion 18 during molding. Referring to FIGS. 19, 20 and 21, various degrees of torque are provided. In FIG. 19, zero degree of torque is provided, thus, slot 16 is inclined at an angle of about 0° with a plane perpendicular to the base. FIG. 20 illustrates a +10° torque designed in the base portion 18 such that is about +10°. FIG. 21 illustrates a −10° torque in the base. It is, of course, that any designed amount of torque may be designed in base portion 18. By placing the torque in the base, the shape and configuration of the tiewings are not affected, thus, no sacrifice in strength is provided in this portion of the product as would be required if the torque was placed in the tiewings. Another advantage of providing torque in the base is the ability to use a single common mold as the tiewings of the bracket leaving the simpler designed base portion of the mold to be varied as needed.

Figure 22:
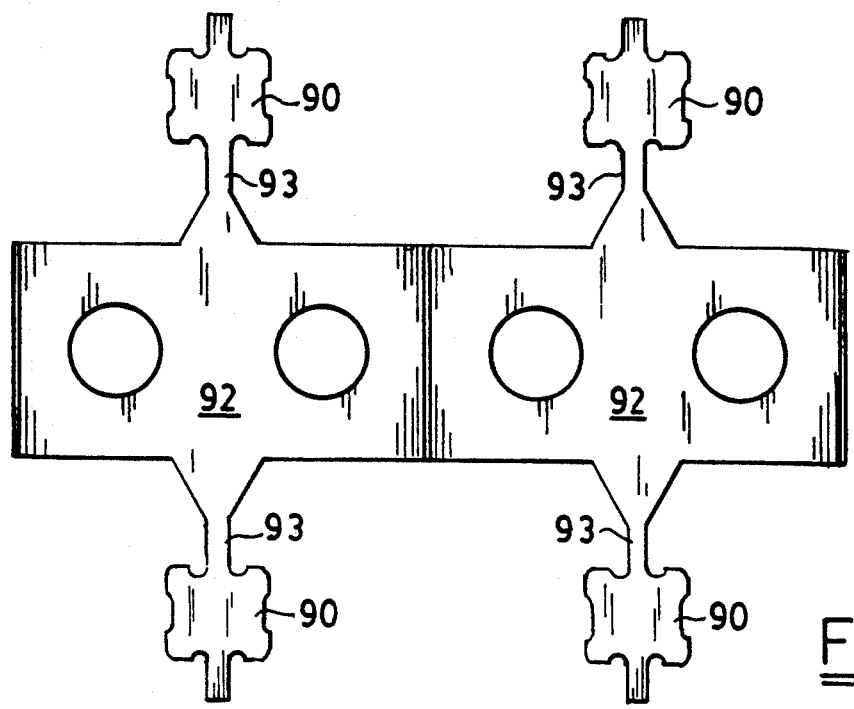
FIG. 22 is a top plan view of how the inserts are initially formed in a blank sheet of metal.
Figure 23:
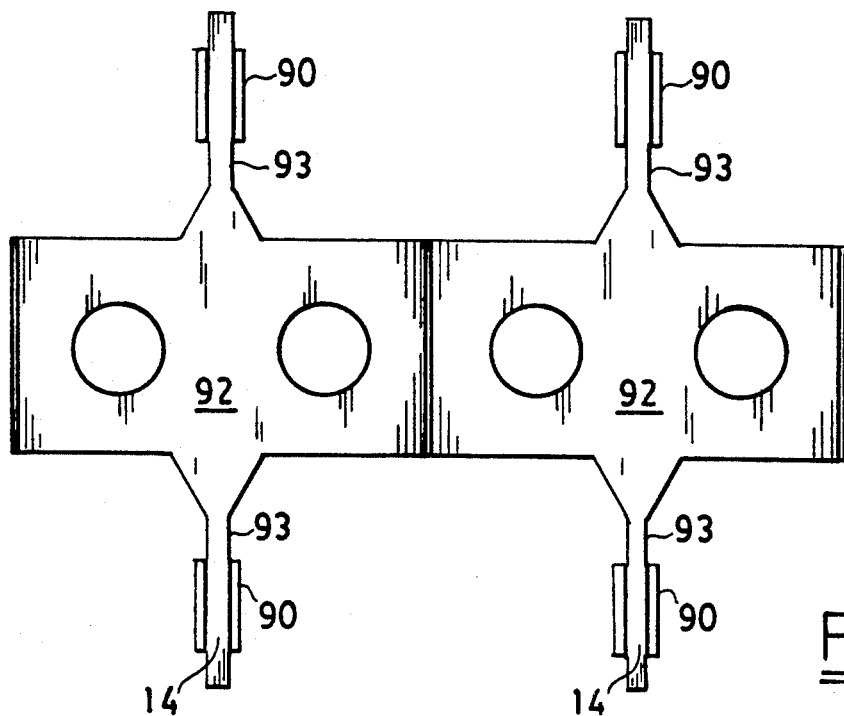
FIG. 23 is a top plan view similar to FIG. 22 with the inserts finally formed.

The brackets 10,110 may be simply made by conventional molding techniques. Preferably, the brackets that are made by injection molding techniques. The inserts are first cut from a sheet of metal so as to form a plurality of blanks 90 which provide the laid out configuration of the base and sidewalls of the insert as shown in FIG. 22. The insert is attached to a main handling section 92 of the blank by a narrow gate 93. In the embodiment illustrated, the gate 93 forms a part of the bottom wall 30 of the insert. The two sidewalls of the insert are folded upwards to form the general U-shaped insert as seen in FIG. 23. The blanks 90 are each placed in an injection mold cavity, the main handling section 92 being outside the cavity of the mold, and plastic material mold around the insert 14 to form body portion 12. The bracket 12 is removed from the mold and is separated from the main handling section at the gate 93 at a predetermined point. Any excess material that is trimmed is removed.

Figure 24:
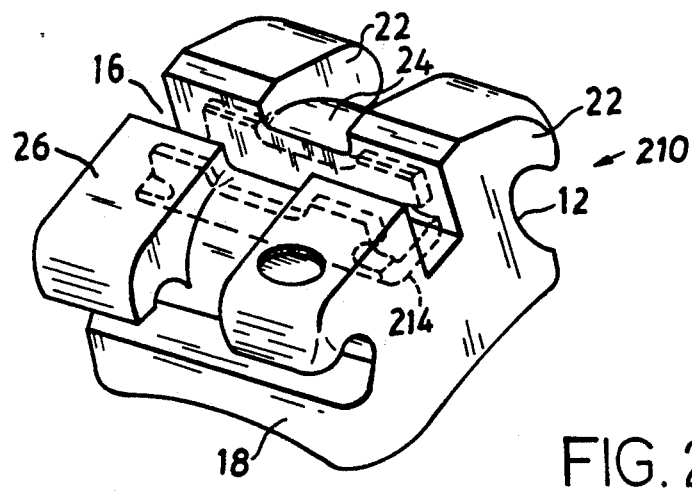
FIG. 24 is a perspective view of a modified orthodontic bracket made in accordance with the present invention.
Figure 25:
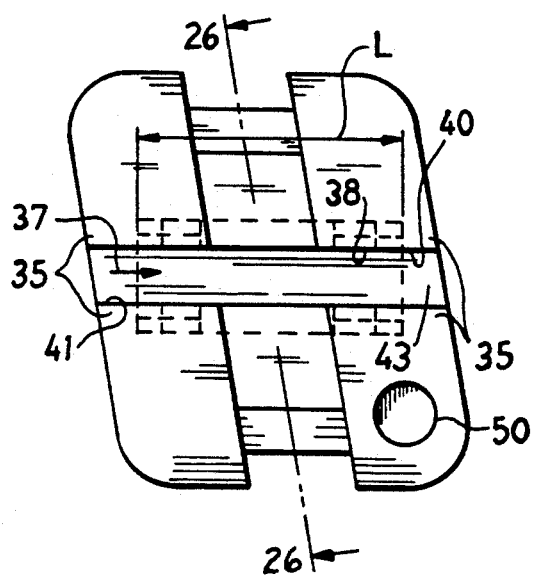
FIG. 25 is a top plan view of the orthodontic bracket of FIG. 24.
Figure 26:
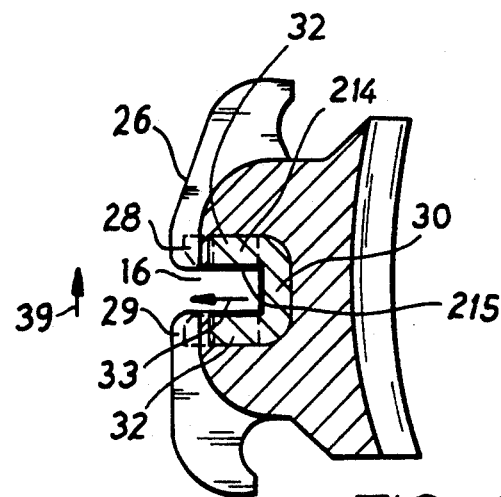
FIG. 26 is a side cross-sectional view of the bracket of FIG. 25 taken along line 25—25.

Referring to FIGS. 24-26 there is illustrated another modified bracket 210 made in accordance with the present invention. Bracket 210 is similar to bracket 10, identical number indicating like parts. In this embodiment reinforcing insert 210 is made of a high strength ceramic material, preferably having aesthetically pleasing qualities. The insert 214 is designed to provide sufficient strength to resist any permanent deformation or breakage due to typical loads applied by the orthodontic archwire. Insert 214, like insert 14 is designed to withstand forces up to about 2-3 lb. range. Insert 214 in the particular embodiment illustrated is made of a stabilized polycrystalline zirconia material which provides a substantially translucent appearance. It is of course understood that various other high strength ceramics or other materials may be employed for the insert. Additionally, tooth colored, transparent or other colored inserts may be used for the desired aesthetic qualities. Insert 210, like insert 10, has a configuration whereby the top surface 28 and ends 35 are covered by cover portions 29, 35, for the same reasons. However, the present invention is not so limited. Additionally, in the embodiment illustrated a thin layer 215 plastic coats the inside surface of the insert 214 which face the slot 16. Thin layer 215 is not too thick as to interfere with the strength provided by insert 214, but is sufficiently thick so as thin to provide a protective coating. In the particular embodiment illustrated layer 215 is about 0.005". This thin layer of plastic reduces the coefficient of friction behind the ceramic insert and archwire and also fully encases the insert further minimizing the potential for leakage of fluid between the insert which assists in and body.

It is to be understood that various changes and modifications may be made without departing from the scope of the present invention. The present invention be limited by the following claims.

We claim:

1. An aesthetically pleasing orthodontic bracket having a strength sufficient to withstand forces, including archwire-applied forces, normally encountered in orthodontic treatment, said bracket comprising a base portion and a body portion extending therefrom, said bracket having at least one tiewing having an archwire slot for receiving an orthodontic archwire, said slot comprising a bottom wall and two opposed sidewalls which extend from said bottom wall, said base portion having a tooth contact surface for mounting the orthodontic bracket to a tooth, said body portion being made of a material selected from the group consisting of substantially transparent and substantially translucent plastics having a filler for improved strength in an amount which does not substantially reduce the transparency or translucency of said transparent or translucent plastic, respectively, said body portion having an insert made of a material having a strength greater than that of said body portion, said insert forming at least a portion of said archwire slot for receiving an orthodontic archwire, said insert comprising a bottom wall which extends along at lest a portion of the length of said slot and a pair of opposing sidewall support sections which form at least a portion of sidewalls of said slot, said insert begin sized and configured so as not to substantially reduce the transparency or translucency of the bracket.

2. An orthodontic bracket according to claim 1 wherein said sidewall support sections of said insert have at least one opening for allowing a portion of said plastic body to extend therethrough so as to restrict movement of said insert in said body.

3. An orthodontic bracket according to claim 2 wherein each of said sidewall support sections each have a substantially U-shaped configuration wherein the open ends of said U-shape configuration are connected to said bottom wall.

4. An orthodontic bracket according to claim 1 wherein said rigid plastic material comprises a polycarbonate plastic being filled with a chopped fiber reinforcement of at least 15% by weight.

5. An orthodontic bracket according to claim 1 wherein said rigid plastic material comprises a polycarbonate plastic being filled with a chopped glass fiber reinforcement of about 20% by weight.

6. An orthodontic bracket according to claim 1 wherein said rigid plastic material having a filler has a tensile strength at yield of at least 13,000 psi.

7. An orthodontic bracket according to claim 1 wherein said rigid plastic material having a filler has a tensile strength at yield of at least 15,000 psi.

8. An orthodontic bracket according to claim 1 wherein said rigid plastic material having a filler has a flex modulus of at least $6.5 \times 10^5$ psi.

9. An orthodontic bracket according to claim 1 wherein said rigid plastic material having a filler has a flex modulus of at $8 \times 10^5$ psi.

10. An orthodontic bracket according to claim 1 wherein said rigid plastic material having a filler has a tensile strength at yield of about 15,000 psi and a flex modulus of about $8 \times 10^5$ psi.

11. An orthodontic bracket according to claim 1 wherein said base portion is made of a rigid material having a filler for improved strength.

12. An orthodontic bracket according to claim 1 wherein said tooth contact surface has been roughened so as to improve the adhesion qualities thereof.

13. An orthodontic bracket according to claim 1 wherein said high strength insert is made of metal.

14. An orthodontic bracket according to claim 13 wherein said insert is made of stainless steel.

15. An orthodontic bracket according to claim 1 wherein the bottom wall of said insert extends beyond the length of said slot in said bracket.

16. An orthodontic bracket according to claim 1 wherein said filler in said rigid plastic material comprises a chopped glass fiber reinforcement.

17. An orthodontic bracket according to claim 1 wherein said insert extends below the top of said body portion.

18. An aesthetically pleasing orthodontic bracket having a strength sufficient to withstand forces, including archwire-applied forces, normally encountered in orthodontic treatment, said bracket comprising a base portion and a body portion extending therefrom, said base portion having a tooth contact surface for mounting the bracket to a tooth, said body portion and base portion being made of a material, selected from the group consisting of substantially transparent ad substantially translucent plastics having a filler for improved strength in an amount which does not substantially reduce the transparency or translucency of said transparent or translucent plastic, respectively, said body portion having an insert made of a material having a strength greater than that of said body portion, said body portion and said insert forming an archwire slot for receiving an orthodontic archwire, said insert having a bottom wall extending along at least a portion of the length of said slot and a pair of oppositely disposed side support sections which extend for at least a portion of the length of said slot, said pair of oppositely disposed side portions each having at least one opening therein for allowing a portion of said body portion to extend therethrough for securing said insert in said body, said insert being sized and configured so as not to substantially reduce the transparency or translucency of the bracket.

19. An orthodontic bracket according to claim 18 wherein said side support sections of said insert have at least one opening for allowing a portion of said plastic body to extend therethrough so as to assist in securing said insert to said body and resist torsional forces tending to cause said insert from coming out of said body portion.

20. An orthodontic bracket according to claim 19 wherein each of said sidewall support sections each have a substantially U-shaped configuration wherein the open ends of said U-shape configuration are connected to said bottom wall.

21. An orthodontic bracket according to claim 18 wherein said rigid plastic material comprises a polycarbonate plastic being filled with a chopped fiber reinforcement of at least 15% by weight.

22. An orthodontic bracket according to claim 18 wherein said rigid plastic material having a filler has a tensile strength at yield of at least 13,000 psi.

23. An orthodontic bracket according to claim 18 wherein said rigid plastic material having a filler has a tensile strength at yield of at least 15,000 psi.

24. An orthodontic bracket according to claim 18 wherein said rigid plastic material having a filler has a flex modulus of at least $6.5 \times 10^5$ psi.

25. An orthodontic bracket according to claim 18 wherein said rigid plastic material having a filler has a flex modulus of at least $8 \times 10^5$ psi.

26. An orthodontic bracket according to claim 18 wherein said rigid plastic material having a filler has a tensile strength at yield of about 15,000 psi and a flex modulus of about $8 \times 10^5$ psi.

27. An orthodontic bracket according to claim 18 wherein said tooth contact surface has been roughened so as to improve the adhesion qualities thereof.

28. An orthodontic bracket according to claim 18 wherein the bottom wall of said insert extends beyond the length of said slot in said bracket.

29. An orthodontic bracket according to claim 18 wherein said filler in said rigid plastic material comprises a glass monofilament material.

30. An orthodontic bracket according to claim 18 wherein said insert extends below the top of said body portion.

31. An orthodontic bracket according to claim 18 wherein said insert is made of metal.

32. An aesthetically pleasing orthodontic bracket having a strength sufficient to withstand forces, including archwire-applied forces, normally encountered in orthodontic treatment, said bracket comprising a base portion with an integral body portion extending therefrom, said bracket having at least one tiewing having a substantially rectangular archwire slot for receiving an orthodontic archwire, said slot comprising a bottom wall and two opposed sidewalls which extend form said bottom wall, said base portion having a tooth contact surface for adhesively mounting the orthodontic bracket to a tooth, said body portion and base portion being made to a material selected form the group consisting of substantially transparent and substantially translucent plastics having a filler for improved strength in an amount which does not substantially reduce the transparency or translucency of said transparent or translucent plastic, respectively, said body portion having a reinforcing insert made of a material having a strength greater than that of said body portion, said inset forming at least a portion of said archwire slot for receiving an orthodontic archwire, said insert comprising a bottom wall which extends along at least a portion of the length of said slot and a pair of opposing sidewall support sections which form at least a portion of sidewalls of said slot, said insert being sized and configured so as not to substantially reduce the transparency or translucency of the bracket.

33. An orthodontic bracket according to claim 32 wherein said rigid plastic material comprises a polycarbonate plastic being filled with a chopped fiber reinforcement of at least 15% by weight.

34. An orthodontic bracket according to claim 32 wherein said rigid plastic material comprises a polycarbonate plastic being filled with a chopped glass fiber reinforcement of about 20% by weight.

35. An orthodontic bracket according to claim 32 wherein said rigid plastic material having a filler has a tensile strength at yield of at least 13,000 psi.

36. An orthodontic bracket according to claim 32 wherein said rigid plastic material having a filler has a tensile strength at yield of at least 15,000 psi.

37. An orthodontic bracket according to claim 32 wherein said rigid plastic material having a filler has a flex modulus of at least $6.5 \times 10^5$ psi.

38. An orthodontic bracket according to claim 32 wherein said rigid plastic material having a filler has a flex modulus of at least $8 \times 10^5$ psi.

39. An orthodontic bracket according to claim 32 wherein said rigid plastic material having a filler has a tensile strength at yield of about 15,000 psi and a flex modulus of about $8 \times 10^5$ psi.

40. An orthodontic bracket according to claim 32 wherein said tooth contact surface has been roughened so as to improve the adhesion qualities thereof.

41. An orthodontic bracket according to claim 32 wherein said filler in said rigid plastic material comprises a chopped glass fiber reinforcement.

42. An orthodontic bracket according to claim 32 wherein said insert extends below the top of said body portion.

43. An orthodontic bracket according to claim 32 wherein said insert is made of a ceramic material.

44. An orthodontic bracket according to claim 32 wherein said insert is made of polycrystalline zirconia.

45. An orthodontic bracket according to claim 32 wherein said insert is made of a ceramic material having a transparent or translucent color.

46. An orthodontic bracket according to claim 32 wherein said insert is made of metal.

* * * * *

REEXAMINATION CERTIFICATE (3972nd)

United States Patent
[19]

Reher et al.

[11] B1 5,254,002

[45] Certificate Issued Jan. 11, 2000

[54] ORTHODONTIC PLASTIC BRACKET

[75] Inventors: James F. Reher, Pomona; Farrokh Farzin-Nia, Inglewood, both of Calif.

[73] Assignee: Ormco Corporation, Glendora, Calif.

Reexamination Requests:
No. 90/004,201, Apr. 2, 1996
No. 90/004,245, May 17, 1996
No. 90/004,658, Jun. 4, 1997

Reexamination Certificate for:
Patent No.: 5,254,002
Issued: Oct. 19, 1993
Appl. No.: 07/682,251
Filed: Apr. 8, 1991

[51] Int. Cl.[7] ............................................ A61C 3/00
[52] U.S. Cl. ..................................................... 433/8
[58] Field of Search ................................. 433/8, 9, 16

[56] References Cited

PUBLICATIONS

The Mirage Advertisement published prior to Sep. 1, 1986 (Journal unknown), as presented by Ormco in its Request to the Food and Drug Adminstratioin for 510(k) Approval on Dec. 8, 1989 ("Mirage reference") for its SPIRIT bracket. The SPIRIT bracket is marketed by ORMCO as its commercial product under the '002 patent.

1990 OIS Orthodontic Brochure for the MAGIC plastic bracket.

1988 OIS Orthodontics Brochure.

*Primary Examiner*—Nicholas D. Lucchesi

[57] ABSTRACT

An orthodontic bracket and method of making same. The bracket comprises a main body portion made of a rigid plastic material having a filler for improved strength. The bracket further includes a rigid reinforcement molded into the body for strengthening the archwire slot. The method comprises forming at least one insert in a blank sheet of metal, forming the insert to its final configuration, placing the insert in a mold cavity and forming the bracket around the insert, removing the bracket from the mold and separating the bracket from the sheet of metal at a predetermined point.

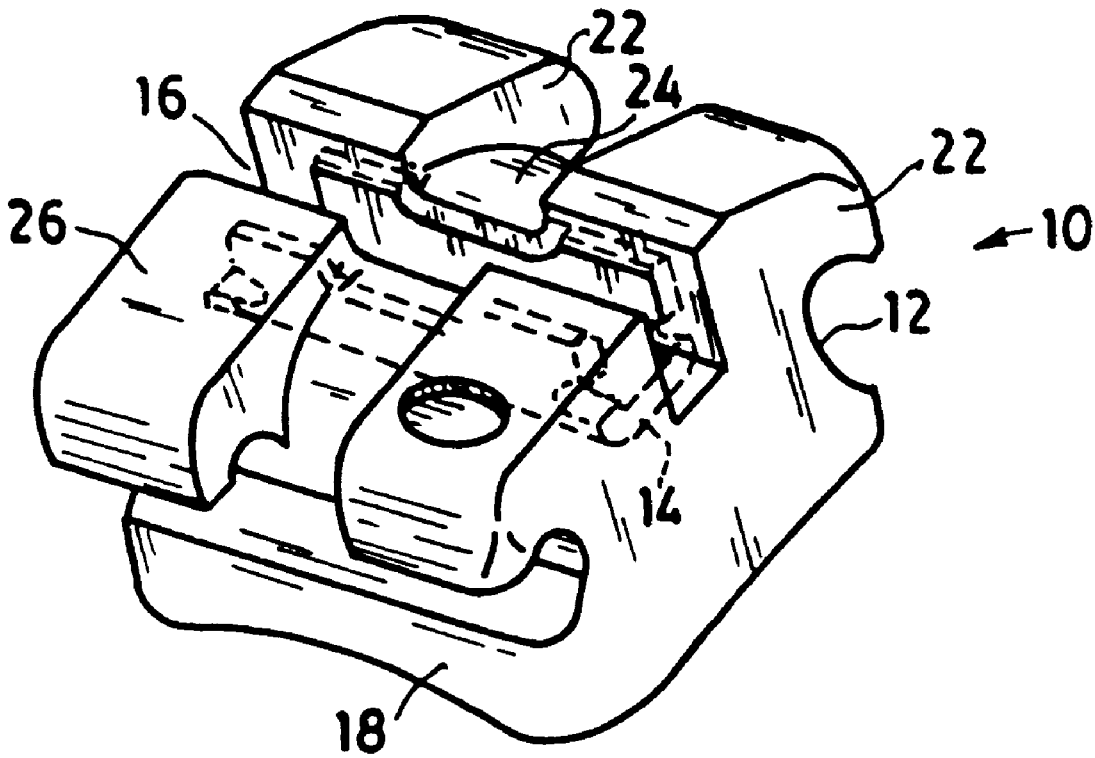

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 4–10, 15, 16, 18, 21–26, 28, 29, 32–39, 41 and 43–45 are determined to be patentable as amended.

Claims 2, 3, 11–14, 17, 19, 20, 27, 30, 31, 40, 42 and 46, dependent on an amended claim, are determined to be patentable.

New claim 47 is added and determined to be patentable.

1. An aesthetically pleasing orthodontic bracket having a strength sufficient to withstand forces, including archwire-applied forces, normally encountered in orthodontic treatment, said bracket comprising a base portion and a body portion extending therefrom, said bracket having at least one tiewing having an archwire slot for receiving an orthodontic archwire, said slot comprising a bottom wall and two opposed sidewalls which extend from said bottom wall, said base portion having a tooth contact surface for mounting the orthodontic bracket to a tooth, said body portion being made of a material selected from the group consisting of substantially transparent and substantially translucent plastics having [a] filler [for improved strength] *present in a structurally utilitarian amount that materially improves the strength of the body portion, said filler present* in an amount which does not substantially reduce the transparency or translucency of said transparent or translucent plastic, respectively, said body portion having an insert made of a material having a strength greater than that of said body portion, said insert forming at least a portion of said archwire slot for receiving an orthodontic archwire, said insert comprising a bottom wall which extends along at least a portion of the length of said slot and a pair of opposing sidewall support sections which form at least a portion of sidewalls of said slot, said insert being sized and configured so as not to substantially reduce the transparency or translucency of the bracket.

4. [An orthodontic bracket according to claim 1] *An aesthetically pleasing orthodontic bracket having a strength sufficient to withstand forces, including archwire-applied forces, normally encountered in orthodontic treatment, said bracket comprising a base portion and a body portion extending therefrom, said bracket having at least one tiewing having an archwire slot for receiving an orthodontic archwire, said slot comprising a bottom wall and two opposed sidewalls which extend from said bottom wall, said base portion having a tooth contact surface for mounting the orthodontic bracket to a tooth, said body portion being made of a material selected from the group consisting of substantially transparent and substantially translucent plastics having a filler for improved strength in an amount which does not substantially reduce the transparency or translucency of said transparent or translucent plastic, respectively, said body portion having an insert made of a material having a strength greater than that of said body portion, said insert forming at least a portion of said archwire slot for receiving an orthodontic archwire, said insert comprising a bottom wall which extends along at least a portion of the length of said slot and a pair of opposing sidewall support sections which form at least a portion of sidewalls of said slot, said insert being sized and configured so as not to substantially reduce the transparency or translucency of the bracket,* wherein said [rigid] plastic material *of said body portion* comprises a polycarbonate plastic [being] filled with [a] chopped fiber reinforcement of at least 15% by weight *filler*.

5. [An orthodontic bracket according to claim 1] *An aesthetically pleasing orthodontic bracket having a strength sufficient to withstand forces, including archwire-applied forces, normally encountered in orthodontic treatment, said bracket comprising a base portion and a body portion extending therefrom, said bracket having at least one tiewing having an archwire slot for receiving an orthodontic archwire, said slot comprising a bottom wall and two opposed sidewalls which extend from said bottom wall, said base portion having a tooth contact surface for mounting the orthodontic bracket to a tooth, said body portion being made of a material selected from the group consisting of substantially transparent and substantially translucent plastics having a filler for improved strength in an amount which does not substantially reduce the transparency or translucency of said transparent or translucent plastic, respectively, said body portion having an insert made of a material having a strength greater than that of said body portion, said insert forming at least a portion of said archwire slot for receiving an orthodontic archwire, said insert comprising a bottom wall which extends along at least a portion of the length of said slot and a pair of opposing sidewall support sections which form at least a portion of sidewalls of said slot, said insert being sized and configured so as not to substantially reduce the transparency or translucency of the bracket,* wherein said [rigid] plastic material *of said body portion* comprises a polycarbonate plastic [being] filled with [a] chopped glass fiber reinforcement of about 20% by weight *filler*.

6. An orthodontic bracket according to claim 1 wherein said rigid plastic material [having a] *has sufficient* filler *such that the filled rigid plastic material* has a tensile strength at yield of at least 13,000 psi.

7. An orthodontic bracket according to claim 1 wherein said rigid plastic material [having a] *has sufficient* filler *such that the filled rigid plastic material* has a tensile strength at yield of at least 15,000 psi.

8. An orthodontic bracket according to claim 1 wherein said rigid plastic material [having a] *has sufficient* filler *such that the filled rigid plastic material* has a flex modulus of at least $6.5 \times 10^5$ psi.

9. An orthodontic bracket according to claim 1 wherein said rigid plastic material [having a] *has sufficient* filler *such that the filled rigid plastic material* has a flex modulus of at least $8 \times 10^5$ psi.

10. An orthodontic bracket according to claim 1 wherein said rigid plastic material [having a] *has sufficient* filler *such that the filled rigid plastic material* has a tensile strength at yield of about 15,000 psi and a flex modulus of about $8 \times 10^5$ psi.

15. [An orthodontic bracket according to claim 1] *An aesthetically pleasing orthodontic bracket having a strength sufficient to withstand forces, including archwire-applied forces, normally encountered in orthodontic treatment, said bracket comprising a base portion and a body portion extending therefrom, said bracket having at least one tiewing having an archwire slot for receiving an orthodontic* archwire, said slot comprising a bottom wall and two opposed sidewalls which extend from said bottom wall, said base portion having a tooth contact surface for mounting the orthodontic bracket to a tooth, said body portion being made of a material selected from the group consisting of substantially transparent and substantially translucent plastics having a filler for improved strength in an amount which does not substantially reduce the transparency or translucency of said transparent or translucent plastic, respectively, said body portion having an insert made of a material having a strength greater than that of said body portion, said insert forming at least a portion of said archwire slot for receiving an orthodontic archwire, said insert comprising a bottom wall which extends along at least a portion of the length of said slot and a pair of opposing sidewall support sections which form at least a portion of sidewalls of said slot, said insert being sized and configured so as not to substantially reduce the transparency or translucency of the bracket, wherein the bottom wall of said insert extends beyond the length of said slot in said bracket.

16. An orthodontic bracket according to claim 1 wherein said filler in said [rigid] plastic material *of said body portion* comprises [a] chopped glass fiber reinforcement.

18. An aesthetically pleasing orthodontic bracket having a strength sufficient to withstand forces, including archwire-applied forces, normally encountered in orthodontic treatment, said bracket comprising a base portion and a body portion extending therefrom, said base portion having a tooth contact surface for mounting the bracket to a tooth, said body portion and base portion being made of a material, selected from the group consisting of substantially transparent and substantially translucent plastics having [a] filler [for improved strength] *present in a structurally utilitarian amount that materially improves the strength of the bracket, said filler present* in an amount which does not substantially reduce the transparency or translucency of said transparent or translucent plastic, respectively, said body portion having an insert made of a material having a strength greater than that of said body portion, said body portion and said insert forming an archwire slot for receiving an orthodontic archwire, said insert having a bottom wall extending along at least a portion of the length of said slot and a pair of oppositely disposed side support sections which extend for at least a portion of the length of said slot, said pair of oppositely disposed side portions each having at least one opening therein for allowing a portion of said body portion to extend therethrough for securing said insert to said body, said insert being sized and configured so as not to substantially reduce the transparency or translucency of the bracket.

21. [An orthodontic bracket according to claim 18] *An aesthetically pleasing orthodontic bracket having a strength sufficient to withstand forces, including archwire-applied forces, normally encountered in orthodontic treatment, said bracket comprising a base portion and a body portion extending therefrom, said base portion having a tooth contact surface for mounting the bracket to a tooth, said body portion and base portion being made of a material, selected from the group consisting of substantially transparent and substantially translucent plastics having a filler for improved strength in an amount which does not substantially reduce the transparency or translucency of said transparent or translucent plastic, respectively, said body portion having an insert made of a material having a strength greater than that of said body portion, said body portion and said insert forming an archwire slot for receiving an orthodontic archwire, said insert having a bottom wall extending along at least a portion of the length of said slot and a pair of oppositely disposed side support sections which extend for at least a portion of the length of said slot, said pair of oppositely disposed side portions each having at least one opening therein for allowing a portion of said body portion to extend therethrough for securing said insert in said body, said insert being sized and configured so as not to substantially reduce the transparency or translucency of the bracket,* wherein said [rigid] plastic material *of said body and base portions* comprises a polycarbonate plastic [being] filled with [a] chopped fiber reinforcement of at least 15% by weight *filler*.

22. An orthodontic bracket according to claim 18 wherein said rigid plastic material [having a] *has sufficient* filler *such that the filled rigid plastic material* has a tensile strength at yield of at least 13,000 psi.

23. An orthodontic bracket according to claim 18 wherein said rigid plastic material [having a ] *has sufficient* filler *such that the filled rigid plastic material* has a tensile strength at yield of at least 15,000 psi.

24. An orthodontic bracket according to claim 18 wherein said rigid plastic material [having a] *has sufficient* filler *such that the filled rigid plastic material* has a flex modulus of at least $6.5 \times 10^5$ psi.

25. An orthodontic bracket according to claim 18 wherein said rigid plastic material [having a] *has sufficient* filler *such that the filled rigid plastic material* has a flex modulus of at least $8 \times 10^5$ psi.

26. An orthodontic bracket according to claim 18 wherein said rigid plastic material [having a] *has sufficient* filler *such that the filled rigid plastic material* has a tensile strength at yield of about 15,000 psi and a flex modulus of about $8 \times 10^5$ psi.

28. [An orthodontic bracket according to claim 18] *An aesthetically pleasing orthodontic bracket having a strength sufficient to withstand forces, including archwire-applied forces, normally encountered in orthodontic treatment, said bracket comprising a base portion and a body portion extending therefrom, said base portion having a tooth contact surface for mounting the bracket to a tooth, said body portion and base portion being made of a material, selected from the group consisting of substantially transparent and substantially translucent plastics having a filler for improved strength in an amount which does not substantially reduce the transparency or translucency of said transparent or translucent plastic, respectively, said body portion having an insert made of a material having a strength greater than that of said body portion, said body portion and said insert forming an archwire slot for receiving an orthodontic archwire, said insert having a bottom wall extending along at least a portion of the length of said slot and a pair of oppositely disposed side support sections which extend for at least a portion of the length of said slot, said pair of oppositely disposed side portions each having at least one opening therein for allowing a portion of said body portion to extend therethrough for securing said insert in said body, said insert being sized and configured so as not to substantially reduce the transparency or translucency of the bracket,* wherein the bottom wall of said insert extends beyond the length of said slot in said bracket.

29. An orthodontic bracket according to claim 18 wherein said filler in said [rigid] plastic material *of said body and base portions* comprises a glass monofilament material.

32. An aesthetically pleasing orthodontic bracket having a strength sufficient to withstand forces, including archwire-applied forces, normally encountered in orthodontic treatment, said bracket comprising a base portion with an integral body portion extending therefrom, said bracket having at least one tiewing having a substantially rectangular archwire slot for receiving an orthodontic archwire, said slot comprising a bottom wall and two opposed sidewalls which extend from said bottom wall, said base portion having a tooth contact surface for adhesively mounting the orthodontic bracket to a tooth, said body portion and base portion being made of a material selected from the group consisting of substantially transparent and substantially translucent plastics having [a] filler [for improved strength] *present in a structurally utilitarian amount that materially improves the strength of the bracket, said filler present* in an amount which does not substantially reduce the transparency or translucency of said transparent or translucent plastic, respectively, said body portion having a reinforcing insert made of a material having a strength greater than that of said body portion, said insert forming at least a portion of said archwire slot for receiving an orthodontic archwire, said insert comprising a bottom wall which extends along at least a portion of the length of said slot and a pair of opposing sidewall support sections which form at least a portion of side walls of said slot, said insert being sized and configured so as not to substantially reduce the transparency or translucency of the bracket.

33. [An orthodontic bracket according to claim 32] *An aesthetically pleasing orthodontic bracket having a strength sufficient to withstand forces, including archwire-applied forces, normally encountered in orthodontic treatment, said bracket comprising a base portion with an integral body portion extending therefrom, said bracket having at least one tiewing having a substantially rectangular archwire slot for receiving an orthodontic archwire, said slot comprising a bottom wall and two opposed sidewalls which extend from said bottom wall, said base portion having a tooth contact surface for adhesively mounting the orthodontic bracket to a tooth, said body portion and base portion being made of a material selected from the group consisting of substantially transparent and substantially translucent plastics having a filler for improved strength in an amount which does not substantially reduce the transparency or translucency of said transparent or translucent plastic, respectively, said body portion having a reinforcing insert made of a material having a strength greater than that of said body portion, said insert forming at least a portion of said archwire slot for receiving an orthodontic archwire, said insert comprising a bottom wall which extends along at least a portion of the length of said slot and a pair of opposing sidewall support sections which form at least a portion of sidewalls of said slot, said insert being sized and configured so as not to substantailly reduce the transparency or translucency of the bracket,* wherein said [rigid] plastic material *of said body and base portions* comprises a polycarbonate plastic [being] filled with [a] chopped fiber reinforcement of at least 15% by weight *filler*.

34. [An orthodontic bracket according to claim 32] *An aesthetically pleasing orthodontic bracket having a strength sufficient to withstand forces, including archwire-applied forces, normally encountered in orthodontic treatment, said bracket comprising a base portion with an integral body portion extending therefrom, said bracket having at least one tiewing having a substantially rectangular archwire slot for receiving an orthodontic archwire, said slot comprising a bottom wall and two opposed sidewalls which extend from said bottom wall, said base portion having a tooth contact surface for adhesively mounting the orthodontic bracket to a tooth, said body portion and base portion being made of a material selected from the group consisting of substantially transparent and substantially translucent plastics hav-*
*ing a filler for improved strength in an amount which does not substantially reduce the transparency or translucency of said transparent or translucent plastic, respectively, said body portion having a reinforcing insert made of a material having a strength greater than that of said body portion, said insert forming at least a portion of said archwire slot for receiving an orthodontic archwire, said insert comprising a bottom wall which extends along at least a portion of the length of said slot and a pair of opposing sidewall support sections which form at least a portion of sidewalls of said slot, said insert being sized and configured so as not to substantially reduce the transparency or translucency of the bracket,* wherein said [rigid] plastic material *of said body and base portions* comprises a polycarbonate plastic [being] filled with [a] chopped glass fiber reinforcement of about 20% by weight *filler*.

35. An orthodontic bracket according to claim 32 wherein said rigid plastic material [having a] *has sufficient* filler *such that the filled rigid plastic material* has a tensile strength at yield of at least 13,000 psi.

36. An orthodontic bracket according to claim 32 wherein said rigid plastic material [having a] *has sufficient* filler *such that the filled rigid plastic material* has a tensile strength at yield of at least 15,000 psi.

37. An orthodontic bracket according to claim 32 wherein said rigid plastic material [having a] *has sufficient* filler *such that the filled rigid plastic material* has a flex modulus of at least $6.5 \times 10^5$ psi.

38. An orthodontic bracket according to claim 32 wherein said rigid plastic material [having a] *has sufficient* filler *such that the filled rigid plastic material* has a flex modulus of at least $8 \times 10^5$ psi.

39. An orthodontic bracket according to claim 32 wherein said rigid plastic material [having a] *has sufficient* filler *such that the filled rigid plastic material* has a tensile strength at yield of about 15,000 psi and a flex modulus of about $8 \times 10^5$ psi.

41. An orthodontic bracket according to claim 32 wherein said filler in said [rigid] plastic material *of said body and base portions* comprises [a] chopped glass fiber reinforcement.

43. [An orthodontic bracket according to claim 32] *An aesthetically pleasing orthodontic bracket having a strength sufficient to withstand forces, including archwire-applied forces, normally encountered in orthodontic treatment, said bracket comprising a base portion with an integral body portion extending therefrom, said bracket having at least one tiewing having a substantially rectangular archwire slot for receiving an orthodontic archwire, said slot comprising a bottom wall and two opposed sidewalls which extend from said bottom wall, said base portion having a tooth contact surface for adhesively mounting the orthodontic bracket to a tooth, said body portion and base portion being made of a material selected from the group consisting of substantially transparent and substantially translucent plastics having a filler for improved strength in an amount which does not substantially reduce the transparency or translucency of said transparent or translucent plastic, respectively, said body portion having a reinforcing insert made of a material having a strength greater than that of said body portion, said insert forming at least a portion of said archwire slot for receiving an orthodontic archwire, said insert comprising a bottom wall which extends along at least a portion of the length of said slot and a pair of opposing sidewall support sections which form at least a portion of sidewalls of said slot, said insert being sized and configured so as not to substantially reduce the transparency or translucency of the bracket,* wherein said insert is made of a ceramic material.

44. An orthodontic bracket according to claim [32] *An aesthetically pleasing orthodontic bracket having a strength sufficient to withstand forces, including archwire-applied forces, normally encountered in orthodontic treatment, said bracket comprising a base portion with an integral body portion extending therefrom, said bracket having at least one tiewing having a substantially rectangular archwire slot for receiving an orthodontic archwire, said slot comprisng a bottom wall and two opposed sidewalls which extend from said bottom wall, said base portion having a tooth contact surface for adhesively mounting the orthodontic bracket to a tooth, said body portion and base portion being made of a material selected from the group consisting of substantially transparent and substantially translucent plastics having a filler for improved strength in an amount which does not substantially reduce the transparency or translucency of said transparent or translucent plastic, respectively, said body portion having a reinforcing insert made of a material having a strength greater than that of said body portion, said insert forming at least a portion of said archwire slot for receiving an orthodontic archwire, said insert comprising a bottom wall which extends along at least a portion of the length of said slot and a pair of opposing sidewall support sections which form at least a portion of sidewalls of said slot, said insert being sized and configured so as not to substantailly reduce the transparency or translucency of the bracket,* wherein said insert is made of polycrystalline zirconia.

45. [An orthodontic bracket according to claim 32] *An aesthetically pleasing orthodontic bracket having a strength sufficient to withstand forces, including archwire-applied forces, normally encountered in orthodontic treatment, said bracket comprising a base portion with an integral body portion extending therefrom, said bracket having at least one tiewing having a substantially rectangular archwire slot for receiving an orthodontic archwire, said slot comprising a bottom wall and two opposed sidewalls which extend from said bottom wall, said base portion having a tooth contact surface for adhesively mounting the orthodontic bracket to a tooth, said body portion and base portion being made of a material selected from the group consisting of substantially transparent and substantially translucent plastics having a filler for improved strength in an amount which does not substantially reduce the transparency or translucency of said transparent or translucent plastic, respectively, said body portion having a reinforcing insert made of a material having a strength greater than that of said body portion, said insert forming at least a portion of said archwire slot for receiving an orthodontic archwire, said insert comprising a bottom wall which extends along at least a portion of the length of said slot and a pair of opposing sidewall support sections which form at least a portion of sidewalls of said slot, said insert being sized and configured so as not to substantially reduce the transparency or translucency of the bracket,* wherein said insert is made of a ceramic material having a transparent or translucent color.

47. *An orthodontic bracket according to claim 1 wherein said filler in said plastic material of said body portion comprises a glass monofilament material.*

* * * * *